United States Patent [19]
Ganz et al.

[11] Patent Number: 5,508,198
[45] Date of Patent: Apr. 16, 1996

[54] STORAGE AND INCUBATION APPARATUS FOR TEMPERATURE SENSITIVE MEDICAL TEST SAMPLES

[76] Inventors: Robert A. Ganz, 1431 Lakeview Ave.; Brian D. Zelickson, 2764 Drew Ave. S., both of Minneapolis, Minn. 55416

[21] Appl. No.: 271,414

[22] Filed: Jul. 6, 1994

[51] Int. Cl.⁶ .................................................... B01L 9/00
[52] U.S. Cl. .................................. 435/303.1; 435/305.2; 422/104; 422/307
[58] Field of Search .......................... 422/99, 104, 307; 435/284, 287, 290, 809, 286.1, 303.1, 305.2

[56] References Cited

U.S. PATENT DOCUMENTS

| | | | |
|---|---|---|---|
| 1,043,561 | 11/1912 | Ayer | 422/104 X |
| 3,562,114 | 2/1971 | Steidl et al. | 435/809 X |
| 4,250,266 | 2/1981 | Wade | 435/809 X |
| 4,384,193 | 5/1983 | Kledzik et al. | 219/521 |
| 4,985,206 | 1/1991 | Bousman et al. | 422/99 |
| 5,266,272 | 11/1993 | Griner et al. | 422/104 |

OTHER PUBLICATIONS helicoView™ Product Literature, Gi Supply (no date).

*Primary Examiner*—Jeffrey R. Snay
*Attorney, Agent, or Firm*—Merchant, Gould, Smith, Edell, Welter & Schmidt

[57] ABSTRACT

A storage and incubation apparatus for temperature sensitive medical test samples includes a clear rack mounted on a base and having a plurality of shelves for supporting one or more test sample slides. The rack includes opposing panels joined by a transverse member and/or a side member, and having an open side defined thereon. The rack is clear to permit viewing of the slides during incubation. Furthermore, a heating element including a thin metal strip is mounted on the interior of the rack directly opposite the test samples to maintain the temperature of the test samples within a narrow predefined range.

16 Claims, 2 Drawing Sheets

FIG.3
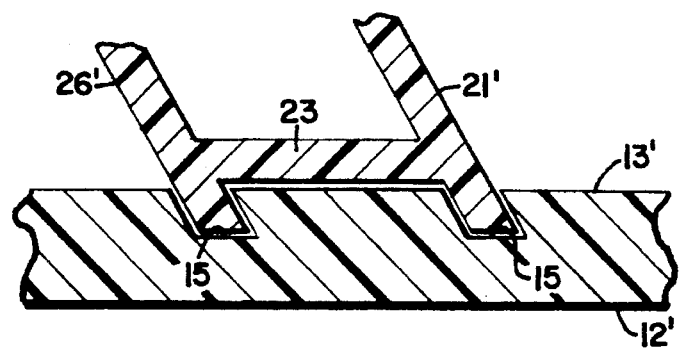
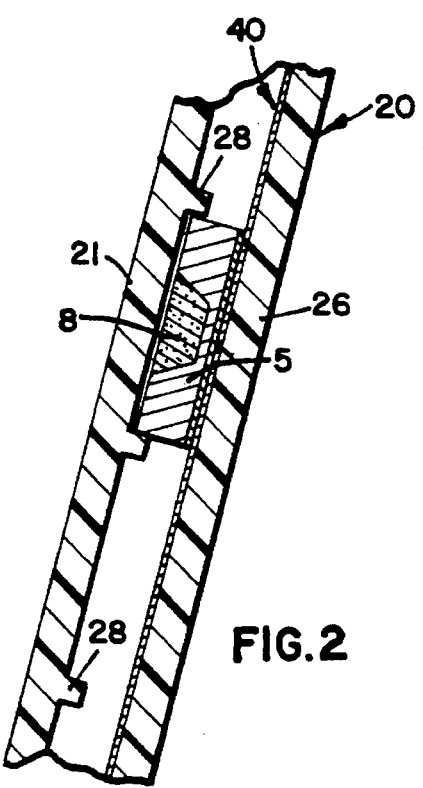
FIG.2

STORAGE AND INCUBATION APPARATUS FOR TEMPERATURE SENSITIVE MEDICAL TEST SAMPLES

FIELD OF THE INVENTION

The invention is directed to a medical storage and incubation apparatus and method, and more particularly is directed to an apparatus and method for storing and incubating temperature-sensitive medical test samples.

BACKGROUND OF THE INVENTION

Enzymatic bacteria culture testing offers a convenient and reliable procedure for detecting the presence of bacteria in a medical test sample. The medical test sample may be a biopsy or blood culture, for example. Other applications of enzymatic bacteria culture testing are also known in the art.

One type of enzymatic test is the CLOtest® H. Pylori Rapid Urease test manufactured by Delta West Pry. Ltd. of Bentley, Australia. In the CLOtest® test procedure, a biopsy specimen is implanted in a test culture disposed in a well on a slide. The presence of bacteria in a specimen is indicated by a color change in the test culture. If bacteria are present, they produce an enzyme which changes the Ph of the culture to induce a color change. If not, then no color change occurs. This procedure thus provides a simple, easy, and definitive visual result indicator.

At room temperature, CLOtest® slides take about 1 to 24 hours to induce a color change. However, the testing time may be reduced to around 1 to 6 hours by incubating the test sample at 20°–40° Celsius (C) (which is roughly equivalent to human body temperature). Furthermore, for the test to be certified, the Clinical Laboratory Improvements Amendment (CLIA) requires the test sample to be maintained at a temperature of 30°–40° C. for three hours.

The conventional manner of heating or incubating enzymatic test samples is to place the samples in a closed unit and maintain the temperature of the samples between 30° and 40° C. Conventional units, however, have several drawbacks. The units must be opened to insert or remove samples, which may cause significant heat loss to the samples, possibly resulting in an invalid test. Further, there is a risk that the cover of a unit may be inadvertently left open during incubation.

In addition, conventional units typically must be opened to view the samples and determine their status. This, however, tends to nullify the primary benefit of the enzymatic tests—a clear visual indicator—since the samples cannot be viewed while being incubated without opening the unit.

Therefore, a need exists for a storage and incubation apparatus for medical test samples which provides simpler, easier and more convenient insertion, removal, incubation and viewing of the medical test samples.

SUMMARY OF THE INVENTION

The invention addresses these and other problems associated with the prior art in providing a storage and incubation apparatus which allows a test sample stored therein to be continuously monitored during incubation. There is no need to open or close the apparatus during incubation, which results in convenient and substantially hands-free test monitoring.

Therefore, according to one aspect of the invention, an apparatus for storing and incubating a temperature sensitive test sample is provided which includes storage means for storing a test sample in a vertical orientation; and incubation means, disposed in the storage means, for incubating the test sample. At least a portion of the storage means is transparent proximate the test sample such that the test sample is visible through the storage means.

According to another aspect of the invention, a method of incubating a temperature sensitive test sample is provided. The method includes the steps of placing a test sample in a vertical orientation in a storage and incubation apparatus, at least a portion of which is transparent proximate the test sample such that the test sample is visible through the apparatus; and incubating the test sample in the apparatus.

In accordance with a further aspect of the invention, an apparatus for storing and incubating a temperature sensitive test sample is provided, which includes a base; a rack, coupled to the base in a generally vertical orientation, for storing at least one test sample in a vertical orientation; and incubation means, disposed in the rack, for incubating the test sample. The rack has an open side defined therein for permitting insertion and removal of the test sample, and at least a portion of the rack is transparent proximate the test sample such that the test sample is visible through the rack.

These and other advantages and features, which define the invention, are set forth below in the claims attached hereto and forming a further part hereof. However, for a better understanding of the invention, and the advantages attained by its use, reference should be made to the Drawing, and to the following descriptive matter, in which there is described a preferred embodiment of the invention.

BRIEF DESCRIPTION OF THE DRAWING

FIG. 2 is a partial fragmentary side cross-sectional view of the preferred storage and incubation apparatus taken along line 2—2 of FIG. 1.

FIG. 3 is an enlarged partial side elevational view of an alternative connection between a rack and a base for a storage and incubation apparatus consistent with the invention.

DETAILED DESCRIPTION OF THE PREFERRED EMBODIMENT

Figure 1:
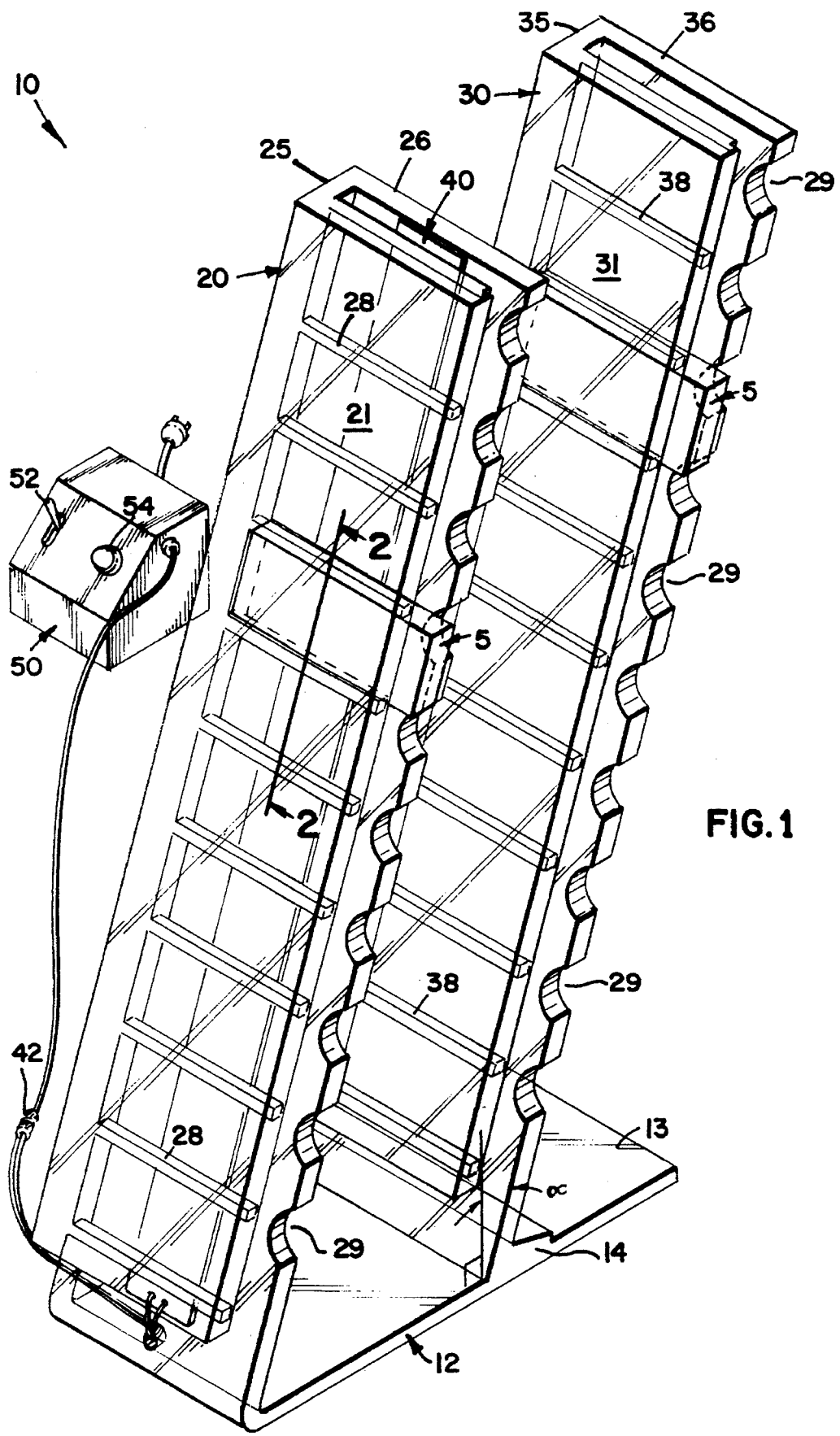
FIG. 1 is a perspective view of a preferred storage and incubation apparatus consistent with the invention.

Turning to the Drawing, wherein like parts are denoted by like numerals throughout the several views, FIGS. 1 and 2 show a preferred storage and incubation apparatus 10 which includes a pair of transparent racks 20, 30 supported in a general vertical orientation on a base 12. Each rack operates as a storage means and includes a plurality of shelves 28 and 38, respectively, for storing test sample slides in a vertical orientation for easy visibility through the rack. Furthermore, an incubation means is provided including a heating element 40 mounted in rack 20 for incubating the slides disposed therein. The incubation means maintains the temperature of the slides within a predetermined range during testing.

Apparatus 10 is preferably used to store and incubate CLOtest® culture slides, such as slide 5 shown in FIG. 2. Slide 5 includes a test specimen 8 implanted in a test culture in a well on the slide. Slide 5 may also have patient or other information on one or both sides thereof. Other known temperature-sensitive slides, cultures and assays may also be stored and incubated in apparatus 10.

The structural components of storage and incubation apparatus 10 are preferably constructed of a clear or translucent plastic material, such as Lucite® plexiglass. The clear plastic construction of the apparatus allows for easy viewing of the slides or other test samples through the apparatus while they are being incubated. Further, to view any information printed on a slide, the configuration of the racks preferably allows both sides of the slides to be viewed through the apparatus. However, it will be appreciated that other plastics or other materials, whether transparent, translucent, or opaque, may be used.

The various components of apparatus 10 are preferably glued together with an adhesive such as methylene chloride. Alternatively, various construction techniques such as plastic welding, injection molding, etc. may be used.

Apparatus 10 includes a base 12 having a top surface 13. The base supports racks 20 and 30 in a generally vertical orientation. Each rack is preferably inclined somewhat toward the rear of the apparatus (i.e., angled with respect to an axis perpendicular to base 12). The inclination (denoted by angle $\alpha$) is preferably between 0 and 30 degrees.

Rack 20 includes opposing front and rear panels 21 and 26 joined by a side panel 25. It will be appreciated that alternate or additional structural support may be provided, e.g. a top panel or a brace proximate the lower portion of rack 20.

A plurality of shelves 28 are mounted on the inner surface of front panel 21 (see FIG. 2). Shelves 28 are lips which extend parallel and vertically spaced apart from one another. Each shelf receives one or more test slides. As discussed above, rack 20 is preferably inclined to the rear of apparatus 10. Further, panels 21 and 26 are spaced from one another at a distance which allows slides 5 to be supported by shelves 28 with test specimens 8 thereon resting against the inner surface of rear panel 26. It will be appreciated that the shelves may alternately be located on the inner surface of rear panel 26, or may fully extend between the panels. It will also be appreciated that the number and spacing of shelves may vary depending upon the size and shape of the particular samples which are stored in the rack.

Rack 20 in the preferred configuration has one side panel 25, while the opposing side is open to permit easy installation and removal of slides from the rack. However, it will be appreciated that both sides could be open, or further, that access doors could be provided on one or both sides for access to the interior of rack 20.

Rear panel 26 preferably extends beyond front panel 21 on the right side thereof, and further includes a number of recesses 29. Panel 26 is preferably similar in width to a slide, while panel 21 is slightly lesser in width, such that the end of the slides project out of the side of rack 20 to facilitate their insertion and removal. It will be appreciated that a similar construction may be provided on the left side of the rack, e.g., for left-handed operation.

A second rack 30 is also preferably included on apparatus 10. Rack 30 is similar in construction to rack 20, including opposing front and rear panels 31 and 36 joined by a transverse member 34. A plurality of shelves 38 are mounted on the inner surface of panel 36, and rack 30 is inclined backward such that the slides resting on the shelves also rest against the inner surface of panel 36.

As shown in FIG. 1, racks 20 and 30 are permanently secured to base 12 through their rear panels 26 and 36, respectively. However, racks 20 and 30 may also be removably supported on base 12. This would enable the racks to be removed for cleaning and disinfecting, and also allow a plurality of different racks to be used with base 12, for example to rotate preloaded racks or to accommodate different sizes and shapes of test samples.

An incubation (or heating) means is also preferably included on apparatus 10 to incubate test samples while they are stored inside the apparatus. The incubation means preferably incubates samples in rack 20, however, it will be appreciated that slides stored in rack 30 could be heated in addition to or in lieu of those in rack 20.

The incubation means includes a heating element 40 which is preferably a thin metal strip in a serpentine pattern bonded to the inner surface of rear panel 26 through a 2 mil thick polyimide self-adhesive backing, for example the Minco No. 9331 HK5168R176L12B heating element manufactured by Minco of Minneapolis, Minn. Heating element 40 is preferably mounted directly opposite to where test samples are mounted on the slides stored in apparatus 10. Typically, this may be accomplished by mounting heating element 40 perpendicular to shelves 28 proximate the center of panel 26. With test slides inserted into rack 20 as shown in FIG. 2, this should orient the samples to rest directly against heating element 40.

Heating element 40 is the type which produces heat when electrical current is passed through the element. Furthermore, this type of heating element may also be used as a temperature sensor because the element has a measurable positive thermal coefficient of resistance. However, it will be appreciated that other known means for providing heat to incubate test samples may also be used.

The heating element 40 is removably connected to a temperature controller 50 through a connector 42. Temperature controller 50 is preferably a Heater-Star controller manufactured by Minco of Minneapolis, Minn. This type of controller is trimmed or adjusted to produce sufficient electrical current through the element to maintain its temperature at about 37° C. The controller includes a feedback mechanism which measures the thermal coefficient of resistance of the heating element to provide closed-loop control over element 40. The use and operation of this type of temperature controller is generally known in the art. It is further known that such temperature controllers are capable of maintaining the temperature of the heating element to within +/–1° C. of the preset temperature.

While temperature controller 50 is shown as a separate unit to the racks and base of apparatus 10, it will be appreciated that different housings may be used, or further, that controller 50 may be mounted directly to or be integral with, the base or racks of apparatus 10.

Depending upon the spacing of the test samples from the element, it is believed that the temperature of the samples will be maintained in the range of 31°–36° C. with a 37° C. heating element. Therefore, it will be appreciated that the spacing between samples and the element, as well as the temperature at which the element is maintained will vary depending upon the preferred temperature range for the samples to be incubated.

Temperature controller 50 is preferably powered by a standard 110 volt outlet, although alternative power sources, such as batteries, may also be used. A power switch 52 is preferably provided to turn the unit on and off, and an indicator light 54 is preferably provided which lights when the heating element reaches operating temperature (set for about 37° C. in the preferred embodiment). The use of such components is also known in the art. Further, it will be appreciated that a temperature setting control may be provided to allow an operator to adjust the temperature of the element for different applications.

It may also be preferable to include a temperature indicator on or in the apparatus to provide a visual indication of the temperature of the test samples. Any conventional thermometer may be used. Alternatively, one or more temperature sensitive materials, such as LCD reversible temperature decals manufactured by Telatemp of Fullerton, CA, may be used to provide inexpensive and reliable temperature verification.

In operation, the incubation means is preferably activated before the racks are loaded to bring it to operating temperature. Next, test slides are inserted into rack 20 such that the test samples disposed thereon rest against heating element 40. The slides are then incubated for a sufficient period of time (typically 3 hours). The status of the samples may be constantly monitored during the incubation of the slides since they are visible through the panels of rack 20. Furthermore, the slides may also be held in unheated rear storage rack 30. Insertion and removal of the slides from racks 20 and 30 is provided through the open side between the opposing panels in each rack.

Several advantages are provided by the preferred apparatus. For instance, it is relatively compact in size and configuration. The apparatus may therefore be used on site, e.g. in a doctor's examining room, and there is consequently no need to send the samples off site to a separate lab for incubation, which provides significant labor and cost savings.

Another advantage of the preferred apparatus is that the slides are vertically arranged in transparent racks, such that the slides are clearly visible even from across a room. Thus, monitoring of the tests' progress is substantially hands-free.

By "vertical orientation", we mean an orientation whereby a test sample is maintained generally vertical with respect to the base such that the sample is clearly viewable through the panels of the racks. For the slides shown in the preferred storage and incubation apparatus 10, this would include the configuration shown in FIG. 1, as well as a configuration whereby the slides are rotated 90° to sit upon their ends. Other configurations of test samples which are easily viewable will vary depending upon the particular test samples involved.

Another advantage of the preferred apparatus 10 is that the open sides in the racks enable easy insertion and removal of slides. No access panels/doors need to be actuated. Further, since the heating is substantially localized proximate the samples themselves, no significant heat loss occurs.

Various alternative embodiments of the preferred storage and incubation apparatus will be appreciated by one of ordinary skill in the art. For example, a greater or fewer number of racks may be provided, all or some of which may include separate heating elements. Also, a greater or lesser number of shelves may be provided in each rack to accommodate more or less slides, and more than one slide may be accommodated per shelf. It will be appreciated that any storage construction which vertically orients test samples and allows for viewing of the samples disposed within the construction during incubation may be used.

An alternative embodiment is shown in FIG. 3, whereby the racks are removably supported in grooves 15 cut into the top surface 13' of base 12' The grooves 15 are preferably angled with respect to a perpendicular axis from top surface 13' to support the racks in a rearwardly inclined fashion. A supplemental cross-brace 23 is also shown for reinforcing the rack, and both panels 21' and 26' are connected to base 12'. Other manners of removably and/or fixably attaching the racks to the base will be appreciated by one skilled in the art. For example, pairs of laterally-extending support rails could be included on the top surface of a base to form channels for supporting one or more panels on each rack.

The invention therefore provides a storage and incubation apparatus which offers increased convenience, reliability and simplicity over many conventional designs. It will be appreciated that various modifications and changes may be made to the preferred embodiment without departing from the spirit in the invention. Therefore, the invention resides solely in the claims hereinafter appended.

We claim:

1. An apparatus for storing and incubating a temperature sensitive test sample, comprising:

(a) storage means for storing a test sample in a vertical orientation, wherein at least a portion of the storage means is transparent proximate the test sample; whereby the test sample is visible through the storage means, and the storage means comprising:

(i) a base; and (ii) a rack coupled to the base in a generally vertical orientation, the rack including a plurality of shelves for receiving a plurality of test samples, wherein the rack comprises front and rear transparent panels coupled along one side thereof by a side panel, wherein the plurality of shelves include a plurality of vertically spaced parallel lips mounted to an inner surface of the front panel, wherein the rack is removably supported in the base, and wherein the rack has an open side defined thereon between the front and rear panels; whereby test samples are inserted and removed from the rack through the open side; and (b) incubation means, disposed in the storage means, for incubating the test sample;

wherein the base comprises two pairs of support members, each pair of support members defining a slot for receiving one of the panels, wherein the support members are angled from an axis perpendicular to the base to rearwardly incline the rack and support the test samples against the inner surface of the rear panel.

2. The apparatus of claim 1, further comprising a second rack coupled to the base in a generally vertical orientation behind the first rack.

3. The apparatus of claim 1, wherein the incubation means comprises a heating element mounted in the rack to heat the test samples to a predetermined temperature.

4. The apparatus of claim 3, wherein the heating element is a thin metal heating element extending generally transverse to the vertically spaced parallel lips and mounted to an inner surface of the rear panel.

5. The apparatus of claim 4, wherein the heating element is bonded to the inner surface of the rear panel through a self-adhesive polyimide backing.

6. The apparatus of claim 4, wherein the heating element is disposed directly opposite the test samples.

7. The apparatus of claim 3, wherein the incubation means further comprises a temperature controller, electrically connected to the heating element, for controlling the heating element to maintain the test samples at 30° to 40° C.

8. The apparatus of claim 7, wherein the heating element has a positive thermal resistance, and wherein controller includes means, responsive to the resistance of the heating element, for maintaining the temperature of the heating element within a predetermined range.

9. An apparatus for storing and incubating a temperature sensitive test sample, comprising:

(a) storage means for storing a test sample in a vertical orientation, wherein at least a portion of the storage means is transparent proximate the test sample; whereby the test sample is visible through the storage means, and the storage means comprising:
(i) a base; and
(ii) a rack coupled to the base in a generally vertical orientation, the rack including a plurality of shelves for receiving a plurality of test samples, wherein the rack comprises front and rear transparent panels coupled along one side thereof by a side panel, wherein the plurality of shelves include a plurality of vertically spaced parallel lips mounted to an inner surface of the front panel, wherein the rack is removably supported in the base, and wherein the rack has an open side defined thereon between the front and rear panels; whereby test samples are inserted and removed from the rack through the open side; and
(b) incubation means, disposed in the storage means, for incubating the test sample;
wherein the base includes a pair of parallel extending slots for receiving the front and rear panels of the rack.

10. The apparatus of claim 9, further comprising a second rack coupled to the base in a generally vertical orientation behind the first rack.

11. The apparatus of claim 9, wherein the incubation means comprises a heating element mounted in the rack to heat the test samples to a predetermined temperature.

12. The apparatus of claim 11, wherein the heating element is a thin metal heating element extending generally transverse to the vertically spaced parallel lips and mounted to an inner surface of the rear panel.

13. The apparatus of claim 12, wherein the heating element is bonded to the inner surface of the rear panel through a self-adhesive polyimide backing.

14. The apparatus of claim 12, wherein the heating element is disposed directly opposite the test samples.

15. The apparatus of claim 11, wherein the incubation means further comprises a temperature controller, electrically connected to the heating element, for controlling the heating element to maintain the test samples at 30° to 40° C.

16. The apparatus of claim 15, wherein the heating element has a positive thermal resistance, and wherein controller includes means, responsive to the resistance of the heating element, for maintaining the temperature of the heating element within a predetermined range.

* * * * *